(12) United States Patent
Pigamo et al.

(10) Patent No.: US 11,242,304 B2
(45) Date of Patent: Feb. 8, 2022

(54) METHOD FOR PRODUCING 1-CHLORO-3,3,3- TRIFLUOROPROPENE

(71) Applicant: Arkema France, Colombes (FR)

(72) Inventors: Anne Pigamo, Pierre-Benite (FR); Cédric Lavy, Pierre-Benite (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 17/053,250

(22) PCT Filed: May 13, 2019

(86) PCT No.: PCT/FR2019/051067
§ 371 (c)(1),
(2) Date: Nov. 5, 2020

(87) PCT Pub. No.: WO2019/220041
PCT Pub. Date: Nov. 21, 2019

(65) Prior Publication Data
US 2021/0238112 A1 Aug. 5, 2021

(30) Foreign Application Priority Data

May 16, 2018 (FR) ...................................... 1854069

(51) Int. Cl.
*C07C 17/20* (2006.01)
*C07C 21/18* (2006.01)

(52) U.S. Cl.
CPC ............ *C07C 21/18* (2013.01); *C07C 17/206* (2013.01)

(58) Field of Classification Search
CPC .................................................... C07C 17/206
See application file for complete search history.

(56) References Cited

U.S. PATENT DOCUMENTS

| | | | |
|---|---|---|---|
| 2,583,812 A | 1/1952 | Briggs et al. |
| 2,882,243 A | 4/1959 | Milton |
| 4,013,566 A | 3/1977 | Taylor |
| 5,616,819 A | 4/1997 | Boyce et al. |
| 5,684,219 A | 11/1997 | Boyce |
| 5,705,779 A | 1/1998 | Demmin et al. |
| 5,877,359 A | 3/1999 | Elsheikh |
| 6,166,274 A | 12/2000 | Bolmer et al. |
| 6,403,847 B1 | 6/2002 | Nakada et al. |
| 8,404,907 B2 | 3/2013 | Nair et al. |
| 8,426,656 B2 | 4/2013 | Merkel et al. |
| 8,436,217 B2 | 5/2013 | Wang et al. |
| 8,704,017 B2 | 4/2014 | Pokrovski et al. |
| 8,877,990 B2 | 11/2014 | Fukuju et al. |
| 9,255,045 B2 | 2/2016 | Pigamo et al. |
| 9,643,903 B2 | 5/2017 | Pokrovski et al. |
| 9,834,499 B2 | 12/2017 | Pigamo et al. |
| 10,077,221 B2 | 9/2018 | Bonnet et al. |
| 10,227,275 B2 | 3/2019 | Pigamo et al. |
| 10,343,963 B2 | 7/2019 | Bonnet |
| 10,427,998 B2 | 10/2019 | Pigamo et al. |
| 10,532,965 B2 | 1/2020 | Pigamo et al. |
| 10,669,465 B2 | 6/2020 | Rached |
| 10,858,561 B2 | 12/2020 | Abbas et al. |
| 11,028,027 B2 | 6/2021 | Wendlinger et al. |
| 11,034,635 B2 | 6/2021 | Wendlinger et al. |
| 11,084,768 B2 | 8/2021 | Wendlinger et al. |
| 2001/0014707 A1 | 8/2001 | Thomas et al. |
| 2010/0191025 A1 | 7/2010 | Perdrieux |
| 2011/0196178 A1 | 8/2011 | Nyberg |
| 2011/0197602 A1 | 8/2011 | Abbas et al. |
| 2011/0201853 A1 | 8/2011 | Tung et al. |
| 2011/0218370 A1 | 9/2011 | Elsheikh et al. |
| 2011/0245549 A1 | 10/2011 | Merkel et al. |
| 2011/0259828 A1 | 10/2011 | Bouvier et al. |
| 2012/0059199 A1 | 3/2012 | Pokrovski et al. |
| 2012/0172636 A1 | 7/2012 | Pokrovski |
| 2012/0190902 A1 | 7/2012 | Nyberg |
| 2012/0226081 A1 | 9/2012 | Elsheikh et al. |
| 2012/0256119 A1 | 10/2012 | Bouvier et al. |
| 2012/0256120 A1 | 10/2012 | Bouvier et al. |
| 2012/0271070 A1 | 10/2012 | Wang et al. |
| 2012/0329893 A1 | 12/2012 | Abbas |
| 2013/0037058 A1 | 2/2013 | Abbas |

(Continued)

FOREIGN PATENT DOCUMENTS

| | | |
|---|---|---|
| CN | 101687735 A | 3/2010 |
| CN | 102216247 A | 10/2011 |

(Continued)

OTHER PUBLICATIONS

U.S. Appl. No. 16/545,294, Anne Pigamo and Bertrand Collier, filed Aug. 20, 2019, (Cited herein as US Patent Application Publication No. 2019/0375698 A1 of Dec. 12, 2019).
U.S. Appl. No. 17/251,328, Kevin Hisler, Anne Pigamo, Laurent Wendlinger and Emmanuel Boussarie, filed Dec. 11, 2020, (Cited herein as US Patent Application Publication No. 2021/0261485 A1 of Aug. 26, 2021).
U.S. Appl. No. 17/280,547, Jean-Christophe Boutier and Wissam Rached, filed Mar. 26, 2021.

(Continued)

*Primary Examiner* — Medhanit W Bahta
(74) *Attorney, Agent, or Firm* — Buchanan Ingersoll & Rooney P.C.

(57) ABSTRACT

The present invention relates to a process for producing 1-chloro-3,3,3-trifluoropropene, comprising the step i) of contacting hydrofluoric acid (HF) in a reactor with a starting composition comprising at least one of the chloro compounds selected from the group consisting of 1,1,3,3-tetrachloropropene (1230za), 1,3,3,3-tetrachloropropene (1230zd) and 1,1,1,3,3-pentachloropropane (240fa), or a mixture thereof, to produce a stream A comprising 1-chloro-3,3,3-trifluoropropene (1233zd), characterized in that said step i) is carried out in a low-HF liquid phase.

10 Claims, No Drawings

(56) References Cited

U.S. PATENT DOCUMENTS

| | | |
|---|---|---|
| 2013/0211154 A1 | 8/2013 | Cottrell et al. |
| 2013/0261353 A1 | 10/2013 | Pokrovski et al. |
| 2013/0261354 A1 | 10/2013 | Merkel et al. |
| 2014/0213831 A1 | 7/2014 | Nyberg |
| 2014/0221704 A1 | 8/2014 | Tung et al. |
| 2014/0264173 A1 | 9/2014 | Merkel et al. |
| 2015/0152235 A1 | 6/2015 | Abbas |
| 2015/0197467 A1 | 7/2015 | Pigamo et al. |
| 2016/0023974 A1 | 1/2016 | Bonnet et al. |
| 2016/0115104 A1 | 4/2016 | Pigamo et al. |
| 2016/0272561 A1 | 9/2016 | Rached et al. |
| 2017/0050904 A1 | 2/2017 | Ondrus |
| 2017/0081263 A1 | 3/2017 | Klausmeyer et al. |
| 2017/0174965 A1 | 6/2017 | Tsuchiya et al. |
| 2017/0210686 A1 | 7/2017 | Pigamo et al. |
| 2018/0015407 A1 | 1/2018 | Vittenet et al. |
| 2018/0093934 A1 | 4/2018 | Pigamo et al. |
| 2018/0148394 A1 | 5/2018 | Pigamo et al. |
| 2018/0346396 A1 | 12/2018 | Pigamo et al. |
| 2018/0354875 A1 | 12/2018 | Bonnet |
| 2019/0048241 A1 | 2/2019 | Abbas et al. |
| 2019/0152883 A1 | 5/2019 | Pigamo et al. |
| 2019/0276721 A1 | 9/2019 | Rached |
| 2019/0375698 A1 | 12/2019 | Pigamo et al. |
| 2020/0407293 A1 | 12/2020 | Wendlinger et al. |
| 2021/0002188 A1 | 1/2021 | Wendlinger et al. |
| 2021/0002189 A1 | 1/2021 | Wendlinger et al. |
| 2021/0261485 A1 | 8/2021 | Hisler et al. |

FOREIGN PATENT DOCUMENTS

| | | |
|---|---|---|
| EP | 0 940 382 A1 | 9/1999 |
| EP | 1 566 600 A1 | 8/2005 |
| EP | 2 035 117 A | 3/2009 |
| FR | 1 257 034 | 1/1960 |
| FR | 2 768 727 A1 | 3/1999 |
| FR | 2 973 717 A1 | 10/2012 |
| FR | 2 973 809 A1 | 10/2012 |
| FR | 3 032 131 A1 | 8/2016 |
| FR | 3 041 632 A1 | 3/2017 |
| JP | 2000-95714 A | 4/2000 |
| JP | 2012-509324 A | 4/2012 |
| WO | 0181353 A1 | 11/2001 |
| WO | WO 2008/127940 A1 | 10/2008 |
| WO | WO 2008/149011 A2 | 12/2008 |
| WO | WO 2008/149011 A3 | 12/2008 |
| WO | WO 2010/059496 A1 | 5/2010 |
| WO | WO 2010/063975 A1 | 6/2010 |
| WO | WO 2010/111067 A1 | 9/2010 |
| WO | WO 2012/067980 A2 | 5/2012 |
| WO | WO 2014/116562 A1 | 7/2014 |
| WO | WO 2015/175791 A1 | 11/2015 |
| WO | WO 2016/146940 A1 | 9/2016 |
| WO | WO 2017/031046 A1 | 2/2017 |

OTHER PUBLICATIONS

U.S. Appl. No. 16/250,141, Anne Pigamo, Laurent Wendlinger, Dominique Duer-Bert, filed Jan. 17, 2019, (Cited herein as US Patent Application Publication No. 2019/0152883 A1 of May 23, 2019).

Ghanem, Akram, et al., "Static mixers; Mechanisms, applications, and characterization methods—A review," Chemical Engineering Research and Design, 2014, pp. 205-228, vol. 92, Elsevier B.V., NL.

Breck, Donald W., et al., "Zeolite Molecular Sieves", John Wiley & Sons Eds, (1974), 159 pages.

Test No. 102: Melting point/Melting range, OECD guidelines for the testing of chemical products, Section 1, OECD Editions, Paris, 1995, available at http://dx.doi.org/10.1787/9789264069534-fr (with English translation) (17 pages).

**Boutier, Jean-Christophe, et al., U.S. Appl. No. 17/280,547 entitled "Stabilization of 1-Chloro-3,3,3-Trifluoropropene," filed in the U.S. Patent and Trademark Office Mar. 26, 2021.

International Search Report (PCT/ISA/210) dated Jul. 30, 2019, by the European Patent Office as the International Searching Authority for International Application No. PCT/FR2019/051067.

Written Opinion (PCT/ISA/237) dated on Jul. 30, 2019, by the European Patent Office as the International Searching Authority for International Application No. PCT/FR2019/051067.

METHOD FOR PRODUCING 1-CHLORO-3,3,3- TRIFLUOROPROPENE

TECHNICAL FIELD OF THE INVENTION

The present invention concerns the production of hydrochlorofluoroolefins. More particularly, the present invention relates to the production of 1-chloro-3,3,3-trifluoropropene.

Technological background of the invention 3,3,3-Trifluoro-1-chloropropene, or alternatively 1-chloro-3,3,3-trifluoropropene (HCFO-1233zd), exists in the form of two isomers: the cis isomer, namely Z-3,3,3-trifluoro-1-chloropropene (HCFO-1233zdZ), and the trans isomer, namely E-3,3,3-trifluoro-1-chloropropene (HCFO-1233zdE). They have different boiling points of, respectively, 18.5° C. for the trans compound and 39.5° C. for the cis compound.

Fluids based on E-3,3,3-trifluoro-1-chloropropene (HCFO-1233zdE) have found numerous applications in varied industrial fields, in particular as heat transfer fluids, propellants, foaming agents, blowing agents, gaseous dielectrics, monomers or polymerization media, support fluids, abrasive agents, drying agents, and fluids for energy production units.

Manufacture of HCFO-1233zdE is accompanied by a multitude of byproducts having a boiling point close to HCFO-1233zdE. This results in purification steps which are relatively complex and costly. The difficulties encountered during the purification of HCFO-1233zdE generally entail an appreciable loss of target product. In addition, the byproducts may form azeotropic compositions with the HCFO-1233zdE, so making it very difficult if not impossible to carry out separation by simple distillation.

There is a process known through U.S. Pat. No. 5,877,359 for preparing HCFO-1233zdE from 1,1,3,3-tetrachloropropene in liquid phase and in the absence of catalyst. The molar HF/1230za ratio in the fluorination reactor is from 12 to 500. There is also a process known, through U.S. Pat. No. 9,643,903, for fluorinating 1,1,3,3-tetrachloropropene in liquid phase and in the absence of catalyst, in an HF-rich medium. A substantial amount of HF present at start-up or in a steady-state regime of an industrial reactor under pressure is undesirable for obvious environmental and safety reasons. The concern for new processes which respect the environment more forms part of an ongoing process of improvement.

Furthermore, a not inconsiderable amount of overfluorinated byproducts are observed, linked to the presence of this HF in large amount. The presence of 245fa may give rise to a loss of yield, it being known that this mixture forms an azeotropic mixture with the primary product, the 1233zdE (see in particular US 2017/174965). It will therefore be difficult to separate and will have to be removed in the form of an azeotropic mixture, so giving rise to a loss of yield.

There is a need, consequently, for new processes which minimize the drawbacks described above.

SUMMARY OF THE INVENTION

According to a first aspect, the present invention provides a process for producing 1-chloro-3,3,3-trifluoropropene, comprising the step i) of contacting hydrofluoric acid (HF) in a reactor with a starting composition comprising at least one of the chloro compounds selected from the group consisting of 1,1,3,3-tetrachloropropene (1230za), 1,3,3,3-tetrachloropropene (1230zd) and 1,1,1,3,3-pentachloropropane (240fa), or a mixture thereof, to produce a stream A comprising 1-chloro-3,3,3-trifluoropropene (1233zd), characterized in that said step i) is carried out in a low-HF liquid phase.

Reducing the amount of HF in the fluorination reactor tends to protect the reactor from corrosion phenomena. Moreover, reducing the amount of HF in the reactor provides an operational reliability which makes the process readily amenable to the industrial scale. The risks of decantation in the liquid-phase reactor are therefore minimized. Additionally, the amount of overfluorinated coproducts is reduced by virtue of the process according to the present invention.

According to one preferred embodiment, said low-HF liquid phase is a liquid phase comprising less than 15% by weight of HF, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said liquid phase.

According to one preferred embodiment, said at least one of the chloro compounds is 1,1,3,3-tetrachloropropene (1230za).

According to one preferred embodiment, said starting composition comprises at least 10% by weight of said at least one of the chloro compounds, based on the total weight of said starting composition.

According to one preferred embodiment, said starting composition comprises less than 10% by weight of HF, based on the total weight of said starting composition.

According to one preferred embodiment, said liquid phase comprises at least 10% by weight of compounds of formula (I) $C_3H_nF_mCl_p$ (I) in which n is an integer from 0 to 8, m is an integer from 0 to 8, and p is an integer from 0 to 8.

According to one preferred embodiment, step i) is carried out in the absence of catalyst.

According to one preferred embodiment, the stream A comprises coproducts selected from the group consisting of 1,3,3,3-tetrafluoropropene and 1,1,1,3,3-pentafluoropropane.

According to one preferred embodiment, the amount of coproducts selected from the group consisting of 1,3,3,3-tetrafluoropropene and 1,1,1,3,3-pentafluoropropane is less than 0.5% by weight, based on the total weight of the stream A at the exit of the reactor.

According to one preferred embodiment, step i) is carried out at a temperature of 50° C. to 150° C.

According to one preferred embodiment, step i) is carried out at a pressure of 5 to 20 bara.

According to a second aspect, the present invention provides a composition comprising at least 98 mol % of (E/Z)-1-chloro-3,3,3-trifluoropropene and less than 0.5 mol % of coproducts selected from the group consisting of 1,3,3,3-tetrafluoropropene and 1,1,1,3,3-pentafluoropropane.

According to one preferred embodiment, the composition comprises at least 99.5 mol % of (E/Z)-1-chloro-3,3,3-trifluoropropene, less than 0.3 mol % of 1,3,3,3-tetrafluoropropene and less than 0.05 mol % of 1,1,1,3,3-pentafluoropropane.

According to one preferred embodiment, said composition is obtained at the exit of a reactor carrying out the process according to the present invention.

DETAILED DESCRIPTION OF THE INVENTION

According to a first aspect of the invention, a process for producing 1-chloro-3,3,3-trifluoropropene is provided. Said process comprises a step i) of contacting hydrofluoric acid (HF) in a reactor with a starting composition comprising at least one of the chloro compounds selected from the group consisting of 1,1,3,3-tetrachloropropene (1230za), 1,3,3,3-tetrachloropropene (1230zd) and 1,1,1,3,3-pentachloropropane (240fa), or a mixture thereof, to produce a stream A comprising 1-chloro-3,3,3-trifluoropropene (1233zd). Said step i) is preferably carried out in a low-HF liquid phase.

As mentioned above, the present process enables production of 1-chloro-3,3,3-trifluoropropene with a high yield and a high selectivity to be obtained. The amount of coproducts in the final reaction mixture is greatly reduced when the present process is carried out in a medium which is low in HF, relative to a process carried out in a medium which is rich in HF. The present invention therefore provides a more efficient process.

According to one preferred embodiment, said starting composition comprises at least 10% by weight of said at least one of the chloro compounds, based on the total weight of said starting composition. Said starting composition advantageously comprises at least 15% by weight of said at least one of the chloro compounds, preferably at least 20% by weight of said at least one of the chloro compounds, more preferably at least 25% by weight of said at least one of the chloro compounds, in particular at least 30% by weight of said at least one of the chloro compounds, more particularly at least 35% by weight of said at least one of the chloro compounds, preferentially at least 40% by weight of said at least one of the chloro compounds, advantageously preferentially at least 45% by weight of said at least one of the chloro compounds, preferably preferentially at least 50% by weight of said at least one of the chloro compounds, particularly preferentially at least 55% by weight of said at least one of the chloro compounds, based on the total weight of said starting composition.

Said starting composition preferably comprises at least 60% by weight or at least 65% by weight or at least 70% by weight or at least 75% by weight or at least 80% by weight or at least 85% by weight or at least 90% by weight or at least 95% by weight or at least 99% by weight of said at least one of the chloro compounds, based on the total weight of said starting composition.

The process according to the present invention is efficient if the starting composition comprises one of said at least one of the chloro compounds at high purity or in a mixture with other organic compounds.

According to one preferred embodiment, said at least one of the chloro compounds is 1,1,3,3-tetrachloropropene (1230za). Said process therefore comprises a step i) of contacting hydrofluoric acid (HF) in a reactor with a starting composition comprising 1,1,3,3-tetrachloropropene (1230za) to produce a stream A comprising 1-chloro-3,3,3-trifluoropropene (1233zd); said step i) is carried out in a low-HF liquid phase as defined above. The present process preferably enables the production of 1-chloro-3,3,3-trifluoropropene in the form of a mixture of the two cis and trans isomers. The present process enables majority production of the trans-1-chloro-3,3,3-trifluoropropene isomer, preferably at least 90 mol % of the trans isomer.

Said starting composition therefore comprises at least 10% by weight of 1,1,3,3-tetrachloropropene, based on the total weight of said starting composition. Said starting composition advantageously comprises at least 15% by weight of 1,1,3,3-tetrachloropropene, preferably at least 20% by weight of 1,1,3,3-tetrachloropropene, more preferably at least 25% by weight of 1,1,3,3-tetrachloropropene, in particular at least 30% by weight of 1,1,3,3-tetrachloropropene, more particularly at least 35% by weight of 1,1,3,3-tetrachloropropene, preferentially at least 40% by weight of 1,1,3,3-tetrachloropropene, advantageously preferentially at least 45% by weight of 1,1,3,3-tetrachloropropene, preferably preferentially at least 50% by weight of 1,1,3,3-tetrachloropropene, particularly preferentially at least 55% by weight of 1,1,3,3-tetrachloropropene, based on the total weight of said starting composition.

Said starting composition preferably comprises at least 60% by weight or at least 65% by weight or at least 70% by weight or at least 75% by weight or at least 80% by weight or at least 85% by weight or at least 90% by weight or at least 95% by weight or at least 99% by weight of 1,1,3,3-tetrachloropropene, based on the total weight of said starting composition.

According to one preferred embodiment, said starting composition comprises less than 15% by weight of HF, based on the total weight of said starting composition, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said starting composition.

In the present process, preferably, the starting composition is devoid of HF. The term "devoid" signifies an amount by weight of less than 500 ppm, preferably less than 100 ppm, more particularly less than 10 ppm.

Carrying out step i) of the present process enables the fluorination of chloro compounds such as 1,1,3,3-tetrachloropropene (1230za), 1,3,3,3-tetrachloropropene (1230zd) or 1,1,1,3,3-pentachloropropane (240fa). Said liquid phase will therefore accumulate fluorinated organic compounds, while maintaining a low HF content therein.

Said low-HF liquid phase is preferably a liquid phase comprising less than 15% by weight of HF, advantageously less than 10% by weight of HF, preferably less than 8% by weight of HF, more preferably less than 6% by weight of HF, in particular less than 5% by weight of HF, more particularly less than 4% by weight of HF, preferentially less than 2% by weight of HF, based on the total weight of said liquid phase.

While step i) is being carried out, said liquid phase may comprise at least 10% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6. Compounds of formula (I) may, for example, be $C_3Cl_6$, $C_3H_4Cl_4$ or $C_3H_3Cl_5$.

Preferably, while step i) is being carried out, said liquid phase may comprise at least 10% by weight of compounds of formula (I) $C_3H_nF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. The compounds of formula (I) may be propane or propene compounds comprising one or more chlorine atoms and/or one or more fluorine atoms. Said liquid phase may preferably comprise at least 10% by weight of compounds of formula (I) selected from the group consisting of $C_3H_2Cl_4$, $C_3H_2C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$. More particularly, said liquid phase may comprise at least 10% by weight of compounds of formula (I) selected from the group consisting of $C_3H_2Cl_4$, $C_3H_2Cl_3F$, and $C_3H_2Cl_2F_2$.

Said liquid phase may comprise at least 15% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6.

More particularly, while step i) is being carried out, said liquid phase may comprise at least 15% by weight of compounds of formula (I) $C_3H_nF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 15% by weight of compounds of formula (I) selected from the group consisting of $C_3H_2Cl_4$, $C_3H_2C_3F$, $C_3H_2Cl_2F_2$, $C_3H_3C_5$, $C_3H_3Cl_4F$, $C_3H_3Cl_3F_2$, and $C_3H_3Cl_2F_3$. More particularly, said liquid phase may comprise at least 15% by weight of compounds of formula (I) selected from the group consisting of $C_3H_2Cl_4$, $C_3H_2C_3F$, and $C_3H_2Cl_2F_2$.

Said liquid phase may comprise at least 20%, at least 30%, at least 40%, at least 50%, at least 60%, at least 70%, at least 80% or at least 90% by weight of compounds of formula (I) $C_3H_nF_mCl_p$ (I) in which n is an integer from 0 to 8, m is an integer from 0 to 8, and p is an integer from 0 to 8; preferably, n is an integer from 0 to 8, m is an integer from 0 to 6, and p is an integer from 0 to 6.

Said liquid phase may comprise at least 20%, at least 30%, at least 40%, at least 50%, at least 60%, at least 70%, at least 80% or at least 90% by weight of compounds of formula (I) $C_3HF_mCl_p$ (I) in which n is an integer from 1 to 8, m is an integer from 0 to 4, and p is an integer from 0 to 4; preferably, n is an integer from 1 to 4, m is an integer from 0 to 3, and p is an integer from 2 to 4. Said liquid phase may preferably comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, $C_3H_2Cl_2F_2$, $C_3H_3Cl_5$, $C_3H_3Cl_4F$, $C_3H_3Cl_3F_2$, and $C_3H_3Cl_2F_3$.

More particularly, said liquid phase may comprise at least 20%, at least 30%, at least 40%, at least 50%, at least 60%, at least 70%, at least 80% or at least 90% by weight of compounds of formula (I) selected from the group consisting of $C_3H_2Cl_4$, $C_3H_2Cl_3F$, and $C_3H_2Cl_2F_2$.

Said liquid phase may also comprise heavy compounds resulting from the dimerization or from the polymerization of the compounds of formula (I) as defined above.

Step i) is preferably carried out in the absence of catalyst.

Step i) may alternatively be carried out in the presence of a catalyst. The catalyst may be a $TiCl_4$ or $SbCl_5$ catalyst. The catalyst may also be an ionic liquid. The ionic liquids which may be suitable are Lewis acid derivatives based on aluminum, titanium, niobium, tantalum, tin, antimony, nickel, zinc or iron. The term "ionic liquids" refers to nonaqueous salts of ionic nature which are liquid at moderate temperatures (preferably below 120° C.). Ionic liquids preferably result from the reaction between an organic salt and an inorganic compound. Ionic liquids are preferably obtained by reaction of at least one halogen or oxyhalogen Lewis acid based on aluminum, titanium, niobium, tantalum, tin, antimony, nickel, zinc or iron with a salt of general formula $Y^+A^-$, in which $A^-$ denotes a halide anion (bromide, iodide and, preferably, chloride or fluoride) or hexafluoroantimonate ($SbF_6$) and $Y^+$ a quaternary ammonium, quaternary phosphonium or ternary sulfonium cation. The halogen Lewis acid based on aluminum, titanium, niobium, tantalum, antimony, nickel, zinc or iron may be a chloro, bromo, fluoro or mixed derivative, for example a chlorofluoro acid. Mention may be made more particularly of the chlorides, fluorides or chlorofluorides having the following formulae:

$TiCl_xF_y$ with $x+y=4$ and $0<=x<=4$ $TaCl_xF_y$ with $x+y=5$ and $0<=x<=5$ $NbCl_xF_y$ with $x+y=5$ and $0<=x<=5$ $SnCl_xF_y$ with $x+y=4$ and $1\le x\le 4$ $SbCl_xF_y$ with $x+y=5$ and $0<=x<=5$ $AlCl_xF_y$ with $x+y=3$ and $0<=x<=3$ $NiCl_xF_y$ with $x+y=2$ and $0<=x<=2$ $FeCl_xF_y$ with $x+y=3$ and $0<=x<=3$ As examples of such compounds, mention may be made of the following compounds: $TiCl_4$, $TiF_4$, $TaCl_5$, $TaF_5$, $NbCl_5$, $NbF_5$, $SbCl_5$, $SbCl_4F$, $SbCl_3F_2$, $SbCl_2F_3$, $SbClF_4$, $SbF_5$, and mixtures thereof. The following compounds are preferentially used: $TiCl_4$, $TaCl_5+TaF_5$, $NbCl_5+NbF_5$, $SbCl_5$, $SbFCl_4$, $SbF_2Cl_3$, $SbF_3Cl_2$, $SbF_4Cl$, $SbF_5$, and $SbCl_5+SbF_5$. The antimony-based compounds are more particularly preferred. As examples of oxyhalogen Lewis acids that may be used according to the invention, mention may be made of $TiOCl_2$, $TiOF_2$ and $SbOCl_xF_y$ (x+y=3). In the salt $Y^+A^-$, the cation $Y^+$ may correspond to one of the following general formulae: $R^1R^2R^3R^4N^+$, $R^1R^2R^3R^4P^+$, $R^1R^2R^3S^+$ in which the symbols $R^1$ to $R^4$, which are identical or different, each denote a saturated or unsaturated, cyclic or noncyclic, or aromatic hydrocarbyl, chlorohydrocarbyl, fluorohydrocarbyl, chlorofluorohydrocarbyl or fluorocarbyl group having from 1 to 10 carbon atoms, with one or more of these groups possibly also containing one or more heteroatoms such as N, P, S or O. The ammonium, phosphonium or sulfonium cation $Y^+$ may also form part of a saturated or unsaturated, or aromatic, heterocycle having from 1 to 3 nitrogen, phosphorus or sulfur atoms, and may correspond to one or other of the following general formulae:

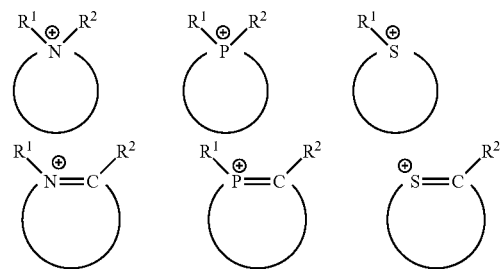

in which $R^1$ and $R^2$ are as defined previously. A salt containing two or three ammonium, phosphonium or sulfonium sites in its formula may also be suitable for use. As examples of salts $Y^+A^-$, mention may be made of tetraalkylammonium chlorides and fluorides, tetraalkylphosphonium chlorides and fluorides, and trialkylsulfonium chlorides and fluorides, alkylpyridinium chlorides and fluorides, dialkylimidazolium chlorides, fluorides and bromides, and trialkylimidazolium chlorides and fluorides. Trimethylsulfonium fluoride or chloride, N-ethylpyridinium chloride or fluoride, N-butylpyridinium chloride or fluoride, 1-ethyl-3-methylimidazolium chloride or fluoride, and 1-butyl-3-methylimidazolium chloride or fluoride are more particularly valued. The ionic liquids may be prepared in a manner known per se by appropriate mixing of the halogen or oxyhalogen Lewis acid and the organic salt $Y^+A^-$. Reference may be made notably to the method described in WO 01/81353. The catalyst may alternatively be triflic or trifluoroacetic acid as stated in U.S. Pat. No. 6,166,274.

According to one preferred embodiment, as well as the 1-chloro-3,3,3-trifluoropropene, the stream A comprises coproducts selected from the group consisting of 1,3,3,3-tetrafluoropropene and 1,1,1,3,3-pentafluoropropane. The 1-chloro-3,3,3-trifluoropropene recovered in said stream A is in the form of a mixture of the two Z and E isomers, as stated above.

According to one preferred embodiment, the amount, in the stream A, of coproducts selected from the group consisting of 1,3,3,3-tetrafluoropropene and 1,1,1,3,3-pentafluoropropane is less than 0.5 mol %. The 1,3,3,3-tetrafluoropropene content of said stream A is preferably less than 0.5 mol %, more preferably less than 0.4 mol %, more particularly less than 0.3 mol %. The 1,1,1,3,3-pentafluoropropane content of said stream A is preferably less than 0.1 mol %, more preferably less than 0.075 mol %, more particularly less than 0.05 mol %.

Said stream A may also comprise HF and HCl.

Step i) is preferably carried out at a temperature of 50° C. to 150° C., preferably at a temperature of 75° C. to 100° C.

Step i) is preferably carried out at a pressure of 5 to 20 bara, preferably at a pressure of 10 to 18 bara, more particularly of 12 to 18 bara.

The molar HF/[chloro compounds] ratio at the entry of the reactor is preferably between 5 and 10, more preferably between 5 and 7, more particularly between 5 and 6. More particularly, when said chloro compound in the starting composition is 1,1,3,3-tetrachloropropene (1230za), the molar HF/1230za ratio is between 5 and 10, more preferably between 5 and 7, more particularly between 5 and 6.

Said process preferably further comprises the steps of: (ii) at least one step of treating the stream A to give a stream B comprising E-1-chloro-3,3,3-trifluoropropene, HCl, HF and Z-1-chloro-3,3,3-trifluoropropene, and a stream C comprising primarily HF (for example at least 50% by weight, preferably at least 70% by weight, of HF); (iii) at least one step of recovering the hydrochloric acid in the stream B, to give a stream D of HCl and a stream E comprising E-1-chloro-3,3,3-trifluoropropene, HCl, HF, and Z-1-chloro-3,3,3-trifluoropropene; (iv) at least one step of purifying the stream E obtained from step (iii) to give E-1233zd, preferably with a purity of not less than 98%, advantageously not less than 99%, and very advantageously not less than 99.9% by weight.

Before the purification step, the stream E obtained in step (iii) is preferably subjected to at least one separation step to give a flow comprising primarily HF (for example, at least 90% by weight, preferably at least 98% by weight, and advantageously at least 99% by weight of HF), which can be recycled to the reactor, and a flow comprising E-1-chloro-3,3,3-trifluoropropene, HCl, HF, and Z-1-chloro-3,3,3-trifluoropropene. The separation step is preferably a decantation, carried out at a temperature advantageously of between −50 and 50° C., preferably between −20° C. and 10° C.

The treatment step (ii) is preferably a reflux column, carried out advantageously at a temperature of between 30 and 120° C. to give the stream C, which is recycled to the reactor.

The recovery of HCl in step (iii) is preferably obtained by means of a distillation column equipped with a bottoms reboiler and a top reflux system. The bottom temperature is advantageously between 20 and 110° C. The overhead temperature is advantageously between −50 and 0° C. The distillation of HCl is typically performed at a pressure of between 7 and 25 bar.

According to one embodiment, the purification step (iv) preferably comprises at least one distillation step and advantageously at least two distillation steps. According to one preferred embodiment, the purification step (iv) comprises at least one step of washing with water and/or washing by means of a basic solution, a drying step, and at least one distillation step. The goal of this distillation step is to remove the light products and also the heavy products, which may be partly recycled to the reactor, depending on whether they are recyclable or not.

The process is preferably carried out continuously.

According to a second aspect, the present invention provides a composition comprising at least 98 mol % of (E/Z)-1-chloro-3,3,3-trifluoropropene and less than 0.5 mol % of coproducts selected from the group consisting of 1,3,3,3-tetrafluoropropene and 1,1,1,3,3-pentafluoropropane. Said composition preferably comprises at least 99 mol % of (E/Z)-1-chloro-3,3,3-trifluoropropene and less than 0.5 mol % of coproducts selected from the group consisting of 1,3,3,3-tetrafluoropropene and 1,1,1,3,3-pentafluoropropane. Said composition more particularly comprises at least 99.5 mol % of (E/Z)-1-chloro-3,3,3-trifluoropropene and less than 0.5 mol % of coproducts selected from the group consisting of 1,3,3,3-tetrafluoropropene and 1,1,1,3,3-pentafluoropropane.

Said composition preferably comprises at least 99 mol % of (E/Z)-1-chloro-3,3,3-trifluoropropene, less than 0.5 mol % of 1,3,3,3-tetrafluoropropene and less than 0.1 mol % of 1,1,1,3,3-pentafluoropropane. Said composition more particularly comprises at least 99 mol % of (E/Z)-1-chloro-3,3,3-trifluoropropene, less than 0.4 mol % of 1,3,3,3-tetrafluoropropene and less than 0.075 mol % of 1,1,1,3,3-pentafluoropropane. Said composition very particularly comprises at least 99 mol % of (E/Z)-1-chloro-3,3,3-trifluoropropene, less than 0.3 mol % of 1,3,3,3-tetrafluoropropene and less than 0.05 mol % of 1,1,1,3,3-pentafluoropropane.

Said composition preferably comprises at least 99.5 mol % of (E/Z)-1-chloro-3,3,3-trifluoropropene, less than 0.3 mol % of 1,3,3,3-tetrafluoropropene and less than 0.05 mol % of 1,1,1,3,3-pentafluoropropane.

According to one preferred embodiment, said composition is obtained at the exit of a reactor carrying out the process according to the present invention.

EXAMPLES

The apparatus used consists of a reactor with a capacity of 60 liters, made of 316L stainless steel. It possesses means for measuring temperature, pressure, and liquid level. The reactants can be fed in via a dip tube, while the products formed circulate through a 5 meter reflux column before being condensed overhead. This column is filled with a structured metal packing which allows the low-boiling-point products to be separated, while the raw material, the intermediate compounds and the unreacted HF drop back into the reactor. A pressure regulation valve imposes an operating pressure on the assembly. An in-line withdrawal system allows the flow of outgoing gas to be sampled, for which it is guided to a gas chromatograph. The reactants are fed in continuously, and the products are analyzed and collected continuously.

Example 1 (Comparative)

An amount of HF of 25 liters is introduced into the reactor. The reactor is maintained at a temperature of 90° C.

The pressure regulation is adjusted to 15 bara. The reactants are then fed in at the following rates: 2 kg/h of HF and 3.5 kg/h of 1230za, giving a molar ratio of the HF to the organic compound of 5.2. The resulting composition of the gas flow after five hours of operation is given in table 1.

Example 2

The procedure of example 1 is reproduced with a start-up amount of 25 liters of a mixture comprising organic compounds and devoid of HF. The mixture comprises an amount by weight of 10.7% of 1230za, 0.9% by weight of 1231 (trichloromonofluoropropene) isomers and 5.7% by weight of 1232 (dichlorodifluoropropene) isomers. The remainder is made up primarily of dimers and of heavy compounds. The reactor is heated in the same way as before, and then the reactants are fed in at the following rates: 2 kg/h of HF and 3.3 kg/h of 1230za, giving a molar ratio of the HF to the organic compound of 5.4. The resulting composition of the gas flow after five hours of operation is given in table 1.

Example 3

The procedure of example 1 is reproduced with a start-up amount of 25 liters of 1230za alone. The reactor is heated in the same way as before, and then the reactants are fed in at the following rates: 1.8 kg/h of HF and 2.9 kg/h of 1230za, giving a molar ratio of the HF to 1230za of 5.6. The resulting composition of the gas flow after five hours of operation is given in table 1.

TABLE 1

| | Molar composition at reactor exit (mol %) | | |
|---|---|---|---|
| | F1233zd-(E/Z) | F1234ze (E + Z) | F245fa |
| Example 1 (comp.) | 98.88% | 0.57% | 0.26% |
| Example 2 | 99.77% | 0.15% | 0.01% |
| Example 3 | 99.56% | 0.26% | 0.01% |

The invention claimed is:

1. A process for producing 1-chloro-3,3,3-trifluoropropene, comprising the step i) of contacting hydrofluoric acid (HF) in a reactor with a starting composition comprising at least one of the chloro compounds selected from the group consisting of 1,1,3,3-tetrachloropropene (1230za), 1,3,3,3-tetrachloropropene (1230zd) and 1,1,1,3,3-pentachloropropane (240fa), or a mixture thereof, to produce a stream A comprising 1-chloro-3,3,3-trifluoropropene (1233zd), wherein said step i) is carried out in a low-HF liquid phase comprising less than 15% by weight of HF, based on the total weight of said liquid phase.

2. The process as claimed in claim 1, wherein said at least one of the chloro compounds is 1,1,3,3-tetrachloropropene (1230za).

3. The process as claimed in claim 1, wherein said starting composition comprises at least 10% by weight of said at least one of the chloro compounds, based on the total weight of said starting composition.

4. The process as claimed in claim 1, wherein said starting composition comprises less than 10% by weight of HF, based on the total weight of said starting composition.

5. The process as claimed in claim 1, wherein said liquid phase comprises at least 10% by weight of compounds of formula (I) $C3H_nF_mCl_p$ (I) in which n is an integer from 0 to 8, m is an integer from 0 to 8, and p is an integer from 0 to 8.

6. The process as claimed in claim 1, wherein step i) is carried out in the absence of catalyst.

7. The process as claimed in any one of the preceding claim 1, wherein the stream A comprises coproducts selected from the group consisting of 1,3,3,3-tetrafluoropropene and 1,1,1,3,3-pentafluoropropane.

8. The process as claimed in claim 1, wherein the amount of coproducts selected from the group consisting of 1,3,3,3-tetrafluoropropene and 1,1,1,3,3-pentafluoropropane is less than 0.5% by weight, based on the total weight of the stream A at the exit of the reactor.

9. The process as claimed in claim 1, wherein step i) is carried out at a temperature of 50° C. to 150° C.

10. The process as claimed in claim 1, wherein step i) is carried out at a pressure of 5 to 20 bara.

* * * * *